United States Patent
Pickett et al.

(10) Patent No.: US 10,796,901 B2
(45) Date of Patent: Oct. 6, 2020

(54) SHELLING OF HALIDE PEROVSKITE NANOPARTICLES FOR THE PREVENTION OF ANION EXCHANGE

(71) Applicant: Nanoco Technologies Ltd., Manchester (GB)

(72) Inventors: Nigel L. Pickett, Manchester (GB); Nathalie C. Gresty, Manchester (GB); Ombretta Masala, Manchester (GB); Jie Li, Manchester (GB)

(73) Assignee: Nanoco Technologies Ltd., Manchester (GB)

(*) Notice: Subject to any disclaimer, the term of this patent is extended or adjusted under 35 U.S.C. 154(b) by 0 days.

(21) Appl. No.: 15/714,519

(22) Filed: Sep. 25, 2017

(65) Prior Publication Data
US 2018/0090312 A1   Mar. 29, 2018

Related U.S. Application Data

(60) Provisional application No. 62/401,485, filed on Sep. 29, 2016, provisional application No. 62/414,110, filed on Oct. 28, 2016.

(51) Int. Cl.
*C09K 11/02* (2006.01)
*H01L 51/00* (2006.01)
(Continued)

(52) U.S. Cl.
CPC ........ *H01L 21/02197* (2013.01); *C09K 11/02* (2013.01); *H01L 33/04* (2013.01);
(Continued)

(58) Field of Classification Search
None
See application file for complete search history.

(56) References Cited

U.S. PATENT DOCUMENTS

| 7,588,828 B2 | 9/2009 | Mushtaq et al. | |
| 2009/0095950 A1* | 4/2009 | Lieber | B82Y 10/00 257/4 |

(Continued)

FOREIGN PATENT DOCUMENTS

| CN | 101003732 A | 7/2007 |
| CN | 104327827 A | 2/2015 |

(Continued)

OTHER PUBLICATIONS

Z. Bai and H. Zhong, Sci. Bull., 2015, 60, 1622.
(Continued)

*Primary Examiner* — Alexander G Ghyka
(74) *Attorney, Agent, or Firm* — Blank Rome LLP

(57) ABSTRACT

A core/shell semiconductor nanoparticle structure comprises a core comprising a halide perovskite semiconductor and a shell comprising a semiconductor material that is not a halide perovskite (and that is substantially free of halide perovskites). The halide perovskite semiconductor core may be of the form $AMX_3$, wherein: A is an organic ammonium such as $CH_3NH_3^+$, $(C_8H_{17})_2(CH_3NH_3)^+$, $PhC_2H_4NH_3^+$, $C_6H_{11}CH_2NH_3^+$ or 1-adamantyl methyl ammonium, an amidinium such as $CH(NH_2)_2^+$, or an alkali metal cation such as $Li^+$, $Na^+$, $K^+$, $Rb^+$ or $Cs^+$; M is a divalent metal cation such as $Mg^{2+}$, $Mn^{2+}$, $Ni^{2+}$, $Co^{2+}$, $Pb^{2+}$, $Sn^{2+}$, $Zn^{2+}$, $Ge^{2+}$, $Eu^{2+}$, $Cu^{2+}$ or $Cd^{2+}$; and X is a halide anion ($F^-$, $Cl^-$, $Br^-$, $I^-$) or a combination of halide anions.

5 Claims, 2 Drawing Sheets

(51) Int. Cl.

| | |
|---|---|
| *H01L 33/04* | (2010.01) |
| *H01L 33/18* | (2010.01) |
| *H01L 51/50* | (2006.01) |
| *H01L 21/02* | (2006.01) |
| *C01D 3/00* | (2006.01) |
| *C07C 211/63* | (2006.01) |
| *C07F 3/00* | (2006.01) |
| *C07F 15/04* | (2006.01) |
| *C07F 15/06* | (2006.01) |

(52) U.S. Cl.
CPC ............ *H01L 33/18* (2013.01); *H01L 51/005* (2013.01); *H01L 51/50* (2013.01); *C01D 3/00* (2013.01); *C01P 2002/34* (2013.01); *C07C 211/63* (2013.01); *C07F 3/00* (2013.01); *C07F 15/04* (2013.01); *C07F 15/06* (2013.01)

(56) References Cited

U.S. PATENT DOCUMENTS

| | | | | |
|---|---|---|---|---|
| 2009/0305231 | A1* | 12/2009 | Weidemaier | B82Y 5/00 435/5 |
| 2012/0064134 | A1* | 3/2012 | Bourke, Jr. | A61Q 17/04 424/401 |
| 2012/0181020 | A1* | 7/2012 | Barron | B01J 13/02 166/250.1 |
| 2017/0153382 | A1 | 6/2017 | Wang et al. | |
| 2017/0233645 | A1 | 8/2017 | Zhong et al. | |
| 2017/0358757 | A1* | 12/2017 | Lee | C09K 11/02 |

FOREIGN PATENT DOCUMENTS

| | | |
|---|---|---|
| CN | 104861958 A | 8/2015 |
| CN | 105349140 A | 2/2016 |
| CN | 105489777 A | 4/2016 |
| CN | 105609643 A | 5/2016 |
| JP | 2017110039 A | 6/2017 |
| WO | 2011036447 A1 | 3/2011 |
| WO | 2013171517 A1 | 11/2013 |
| WO | 2016126211 A1 | 8/2016 |

OTHER PUBLICATIONS

G. Nedelcu, L. Protesescu, S. Yakunin, M.I. Bodnarchuk, M.J. Grotevent and M.V. Kovalenko, Nano Lett., 2015, 15, 563.

S. Pathak, N. Sakai, F.W.R. Rivarola, S.D. Stranks, J. Liu, G.E. Eperon, C. Ducati, K. Wojciechowski, J.T. Griffiths, A.A. Haghighirad, A. Pelleroque, R.H. Friend and H.J. Snaith, Chem. Mater., 2015, 27, 8066.

Q.A. Akkermann, V. D'Innocenzo, S. Accornero, A. Scarpellini, A. Petrozza, M. Prato and L. Manna, J. Am. Chem. Soc., 2015, 137, 10276.

S. Bhaumik, S.A. Veldhuis, Y.F. Ng, M. Li, S.K. Muduli, T.C. Sum, B. Damodaran, S. Mhaisalkar and N. Mathews, Chem. Commun., 2016, 52, 7118.

S. Halim, High Performance Cadmium-Free QD Formulations for LCD Backlight Films, presented at SID Display Week, San Francisco, California, May 24-26, 2016. http://nanograde.com/wp-content/uploads/2016/06/Nanograde_QD_SID_Talk.pdf.

Q. Zhou, Z. Bai, W.-G. Lu, Y. Wang, B. Zou and H. Zhong, Adv. Mater., 2016, ahead of print, DOI: 10.1002/adma.201602651.

S.A. Veldhuis, P.P. Boix, N. Yantara, M. Li, T.C. Sum, N. Mathews and S.G. Mhaisalkar, Adv. Mater., 2016, 28, 6804.

L. Lang, J.-H. Yang, H.-R. Liu, H.J. Xiang and X.G. Gong, Phys. Lett. A, 2014, 378, 290.

P.N. Oliveira, D. Alanis, R.D. Bini, D.M. Silva, G.S. Dias, I.A. Santos, L.F. Cótica, R. Guo and A.S. Bhalla, Integrated Ferroelectric, 2016, 171, 88.

H.C. Yoon, H. Kang, S. Lee, J.H. Oh, H. Yang and Y.R. Do, ACS Appl. Mater. Interfaces, 2016, 8, 18189.

International Search Report issued in copending PCT Application No. PCT/IB2017/055869, dated Jan. 17, 2018, 9 pages.

ROC Tawan Patent Search Report issued in copending TW Application No. 106133587, dated May 9, 2018, 1 page.

De Roo, Jonathan et al.; "Highly Dynamic Ligand Binding and Light Absorption Coefficient of Cesium Lead Bromide Perovskite Nanocrystals"; ACS Nano; 2016; 10; pp. 2071-2081.

De Roo, Jonathan et al.; "Supporting Information for: Highly Dynamic Ligand Binding at the Surface of Cesium Lead Halide Perovskite Nanocrystals"; ACS Nano; 2016; pp. S1-S11.

* cited by examiner

SHELLING OF HALIDE PEROVSKITE NANOPARTICLES FOR THE PREVENTION OF ANION EXCHANGE

CROSS-REFERENCE TO RELATED APPLICATIONS

This application claims the benefit of U.S. Provisional Application Ser. No. 62/401,485 filed on Sep. 29, 2016, and U.S. Provisional Application Ser. No. 62/414,110 filed on Oct. 28, 2016, the contents of which are hereby incorporated by reference in their entireties.

STATEMENT REGARDING FEDERALLY SPONSORED RESEARCH OR DEVELOPMENT

Not Applicable

BACKGROUND OF THE INVENTION

1. Field of the Invention

The present invention generally relates to semiconductor nanoparticles (or "quantum dots"). More particularly, it relates to halide perovskite nanocrystals.

2. Description of the Related Art Including Information Disclosed Under 37 CFR 1.97 and 1.98

Perovskites, materials that exhibit the same crystal structure as calcium titanium oxide ($CaTiO_3$), display a variety of interesting properties that have been explored for technological applications. Generally, perovskites take the form $ABX_3$, where A and B are cations having substantially different sizes and X is an anion that bonds to both A and B.

Halide perovskite nanoparticles of the form $AMX_3$, where A is an organic ammonium (e.g. $CH_3NH_3^+$) or alkali metal cation (e.g. $Li^+$, $Na^+$, $K^+$, $Rb^+$, $Cs^+$), M is a divalent metal cation (e.g. $Mg^{2+}$, $Mn^{2+}$, $Pb^{2+}$, $Sn^{2+}$, $Zn^{2+}$), and X is a halide anion (e.g. $F^-$, $Cl^-$, $Br^-$, $I^-$), have received considerable interest owing to the properties of the materials, which have been found to be particularly suitable for photovoltaic and luminescence applications. In particular, nanoparticles of $CH_3NH_3PbX_3$ and $CsPbX_3$ (X=Cl, Br, I), can be tuned to photoluminesce across the visible spectrum with high quantum yields (QYs; as high as about 90%) and narrow full-widths at half-maximum (FWHM; typically about 20-40 nm) by varying the halide composition. As such, halide perovskite nanoparticles are being investigated for display applications, such as their incorporation into the backlight unit (BLU) of liquid crystal displays (LCDs). [Z. Bai and H. Zhong, Sci. Bull., 2015, 60, 1622] However, one drawback of halide perovskite nanoparticles is that the halides undergo rapid anion exchange when combined [G. Nedelcu, L. Protesescu, S. Yakunin, M. I. Bodnarchuk, M. J. Grotevent and M. V. Kovalenko, Nano Lett., 2015, 15, 5635], leading to loss of the individual PL emissions, [S. Pathak, N. Sakai, F. W. R. Rivarola, S. D. Stranks, J. Liu, G. E. Eperon, C. Ducati, K. Wojciechowski, J. T. Griffiths, A. A. Haghighirad, A. Pelleroque, R. N. Friend and H. J. Snaith, Chem. Mater., 2015, 27, 8066]. [Q. A. Akkermann, V. D'Innocenzo, S. Accornero, A. Scarpellini, A. Petrozza, M. Prato and L. Manna, J. Am. Chem. Soc., 2015, 137, 10276] This presents a significant challenge when aiming to combine a blue light-emitting diode (LED) excitation source with green- and red-emitting halide perovskite nanoparticles in an LCD BLU.

In the synthesis of quantum dots (QDs), overcoating a "core" semiconductor material with a "shell" of a wider band gap semiconductor material is a method commonly used to eliminate surface defects and dangling bonds that lead to non-radiative electron-hole recombination and thus lower QY. Since halide perovskite core nanoparticles display high QYs, core/shell halide perovskite nanoparticle structures have been little investigated. To the best of Applicants' knowledge, the only investigation into core/shell halide perovskite nanoparticles is a report from Bhaumik and co-workers, [S. Bhaumik, S. A. Veldhuis, Y. F. Ng, M. Li, S. K. Muduli, T. C. Sum, B. Damodaran, S. Mhaisalkar and N. Mathews, Chem. Commun., 2016, 52, 7118] who shelled a core of $CH_3NH_3PbBr_3$ with $(C_8H_{17})_2(CH_3NH_3)PbBr_2$ in order to investigate the properties afforded by shelling with a wider band gap organo-halide perovskite. However, there have been no reports of the use of a semiconductor shell to act as a barrier to prevent migration of the halide anion in halide perovskite nanoparticles. Bhaumik et al. described the shelling of a core of $CH_3NH_3PbBr_3$ with $(C_8H_{17})_2PbBr_2$ in order to investigate the properties afforded by shelling with a wider band gap, organo-halide perovskite. [S. Bhaumik, S. A. Veldhuis, Y. F. Ng, M. Li, S. K. Muduli, T. C. Sum, B. Damodaran, S. Mhaisalkar and N. Mathews, Chem. Commun., 2016, 52, 7118] However, the presence of halide ions in both the core and the shell suggests that anion exchange between nanoparticles comprising different halide ions would not be mitigated by the shell layer.

Pathak et al. reported that anion exchange between (OA: MA)$PbX_3$ (OA=octylammonium; MA=methylammonium; X=$Cl^-$; $Br^-$; $I^-$) nanocrystals with different halide compositions could be prevented by individually mixing solutions of the halide perovskite nanocrystals with different compositions with polystyrene beads, then mixing the individual solutions together and processing to form a film. [Id.] This approach requires additional processing to form polymer solutions for each color, as compared to an approach wherein all colors of nanoparticles can be combined in a single processing step.

The nanoparticle manufacturer Nanograde Ltd. (Staefa, Switzerland) has addressed the issue of anion exchange in LCD backlight units comprising red-emitting and green-emitting halide perovskite nanocrystals by separately encapsulating the red- and the green-emitting nanoparticles in a polymer, prior to their incorporation into a resin matrix. [S. Halim, *High Performance Cadmium-Free QD Formulations for LCD Backlight Films*, presented at SID Display Week, San Francisco, Calif., 24-26 May, 2016. http://nanograde-.com/wp-content/uploads/2016/06/Nanograde_QD_SID-_Talk.pdf]. The method has been used to prepare BLUs displaying a color gamut of 108% area of the National Television Systems Committee (NTCS) standard in the Commission Internationale de l'Eclairage 1976 (CIE 1976) color space. However, this method requires separate processing of the red- and the green-emitting nanoparticles into the polymer matrix, thereby adding a processing step as compared to a method wherein the red- and the green-emitting nanoparticles are combined in a single polymer matrix.

Green-emitting $CH_3NH_3PbBr_3$ nanoparticles have been used in combination with red $K_2SiF_6:Mn^{4+}$ (KSF) phosphor and a blue InGaN LED to form a backlight displaying 121% of the NTSC color standard (100% coverage) in the CIE 1931 color space. [Q. Zhou, Z. Bai, W.-G. Lu, Y. Wang, B. Zou and H. Zhong, Adv. Mater., 2016, ahead of print, DOI: 10.1002/adma.201602651] The nanoparticles were embedded in a polyvinylidene fluoride (PVDF) matrix and the KSF was incorporated into an adhesive layer. One drawback of this method is that the nanoparticles and the phosphor layer need to be processed separately, adding to the processing time and cost. It was also noted that the composite films were not stable above 70° C.

Thus, there is a need for a simple method to combine different halide perovskite nanoparticles while preventing anion exchange.

BRIEF SUMMARY OF THE INVENTION

A core/shell semiconductor nanoparticle structure is disclosed that comprises a core comprising a halide perovskite semiconductor and a shell comprising a semiconductor material that is not a halide perovskite (and that is substantially free of halide perovskites), as shown in FIG. 1. The halide perovskite semiconductor core may be of the form $AMX_3$, wherein: A is an organic ammonium such as, but not restricted to, $CH_3NH_3^+$, $(C_8H_{17})_2(CH_3NH_3)^+$, $PhC_2H_4NH_3^+$, $C_6H_{11}CH_2NH_3^+$ or 1-adamantyl methyl ammonium, an amidinium such as, but not restricted to, $CH(NH_2)_2^+$, or an alkali metal cation such as, but not restricted to, $Li^+$, $Na^+$, $K^+$, $Rb^+$ or $Cs^+$; M is a divalent metal cation such as, but not restricted to, $Mg^{2+}$, $Mn^{2+}$, $Ni^{2+}$, $Co^{2+}$, $Pb^{2+}$, $Sn^{2+}$, $Zn^{2+}$, $Ge^{2+}$, $Eu^{2+}$, $Cu^{2+}$ or $Cd^{2+}$; and X is a halide anion ($F^-$, $Cl^-$, $Br^-$, $I^-$) or a combination of halide anions. The shell may act as a barrier to prevent migration of the halide anion(s) from the core, thus preventing anion exchange when more than one type of halide perovskite nanoparticle are combined in a solution or matrix. The invention is particularly suitable for combining different colors of nanoparticles for use in display devices.

BRIEF DESCRIPTION OF THE SEVERAL VIEWS OF THE DRAWING(S)

DETAILED DESCRIPTION OF THE INVENTION

Figure 1:
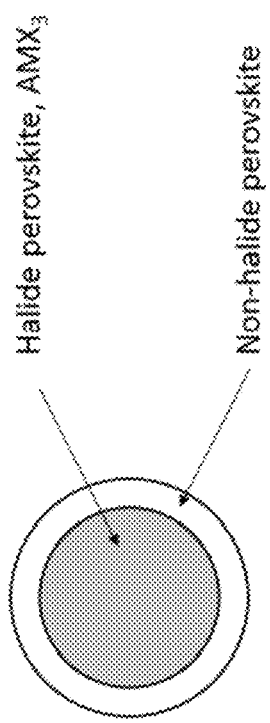
FIG. 1 is a cross-sectional view showing the structure of certain core/shell nanocrystals according to the invention.

Herein, core/shell nanoparticles comprising a halide perovskite semiconductor core and a semiconductor shell of a material other than a halide perovskite are described, wherein the shell may act as a barrier to prevent migration of the halide anion(s) from the core, thus preventing anion exchange when more than one type of halide perovskite nanoparticle are combined in a solution or matrix. A cross-sectional view of the structure of such core/shell nanoparticles is shown in FIG. 1. The invention is particularly suitable for combining different colors of nanoparticles for use in display devices.

As used herein, the term "halide perovskite" means a material of the form $AMX_3$, where A is an organic ammonium such as, but not restricted to, $CH_3NH_3^+$, $(C_8H_{17})_2(CH_3NH_3)^+$, $PhC_2H_4NH_3^+$, $C_6H_{11}CH_2NH_3^+$ or 1-adamantyl methyl ammonium, an amidinium such as, but not restricted to, $CH(NH_2)_2^+$, or an alkali metal cation such as, but not restricted to, $Li^+$, $Na^+$, $K^+$, $Rb^+$ or $Cs^+$; M is a divalent metal cation such as, but not restricted to, $Mg^{2+}$, $Mn^{2+}$, $Ni^{2+}$, $Co^{2+}$, $Pb^{2+}$, $Sn^{2+}$, $Zn^{2+}$, $Ge^{2+}$, $Eu^{2+}$, $Cu^{2+}$ or $Cd^{2+}$; and X is a halide anion ($F^-$, $Cl^-$, $Br^-$, $I^-$) or a combination of halide anions.

The halide perovskite nanocrystal cores may be synthesised by any method. The synthesis of halide perovskite nanocrystals is well known in the prior art. For instance, colloidal syntheses of halide perovskite nanocrystals have been reviewed by Veldhuis et al. [S. A. Veldhuis, P. P. Boix, N. Yantara, M. Li, T. C. Sum, N. Mathews and S. G. Mhaisalkar, Adv. Mater., 2016, 28, 6804] For organo-halide perovskite nanocrystals (for example where A is an ammonium ion), synthesis is typically conducted below about 80° C., via a ligand-assisted re-precipitation method. Here, polar solvents that can dissolve inorganic lead and ammonium halide salts are injected into a polar solvent in the presence of coordinating ligands that stabilize the nanoparticles. $CsPbX_3$ nanocrystals are typically synthesized by hot-injection at temperatures above about 150° C.

In some embodiments, the core/shell nanocrystal comprises a shell of a wider band gap semiconductor material. Table 1 shows the band gap of various halide perovskite semiconductors, as determined by ab initio calculations. [L. Lang, J.-H. Yang, H.-R. Liu, H. J. Xiang and X. G. Gong, Phys. Lett. A, 2014, 378, 290]

TABLE 1

| | $E_g$, eV | | |
|---|---|---|---|
| | X = Cl | X = Br | X = I |
| $CH_3NH_3SnX_3$ | 1.94 | 1.31 | 0.75 |
| $CH_3NH_3PbX_3$ | 1.98 | 1.48 | 0.95 |
| $CsSnX_3$ | 1.19 | 0.80 | 0.49 |
| $CsPbX_3$ | 1.83 | 1.32 | 0.86 |

In some embodiments, the shell material comprises a perovskite crystal structure but does not comprise halide ions, such that the core and shell share a compatible crystallographic phase or similar lattice type to facilitate epitaxial growth of the shell layer and to minimize lattice strain at the core/shell interface. Suitable materials include, but are not restricted to: $BaTiO_3$, $SrTiO_3$, $BiFeO_3$, $LaNiO_3$, $CaTiO_3$, $PbTiO_3$ and $LaYbO_3$. The shelling of nanoparticles with materials such as $BaTiO_3$ has been described in the prior art. [P. N. Oliveira, D. Alanis, R. D. Bini, D. M. Silva, G. S. Dias, I. A. Santos, L. F. Cótica, R. Guo and A. S. Bhalla, Integrated Ferroelectrics, 2016, 174, 88]

In other embodiments, the shell material comprises a semiconductor that does not comprise the perovskite crystal structure. Suitable materials include, but are not restricted to:

IIA-VIB (2-16) material, incorporating a first element from group 2 of the periodic table and a second element from group 16 of the periodic table and also including ternary, quaternary and higher order materials and doped materials, such as, but not restricted to: MgS, MgSe, MgTe, CaS, CaSe, CaTe, SrS, SrSe, SrTe;

IIB-VIB (12-16) material incorporating a first element from group 12 of the periodic table and a second element from group 16 of the periodic table and also including ternary, quaternary and higher order materials and doped materials, such as, but not restricted to: ZnS, ZnSe, ZnTe, CdS, CdSe, CdTe, HgS, HgSe, HgTe;

II-V material incorporating a first element from group 12 of the periodic table and a second element from group 15 of the periodic table and also including ternary, quaternary and higher order materials and doped materials, such as, but not restricted to: $Zn_3P_2$, $Zn_3As_2$, $Cd_3P_2$, $Cd_3As_2$, $Cd_3N_2$, $Zn_3N_2$;

III-V material incorporating a first element from group 15 of the periodic table and a second element from group 15 of the periodic table and also including ternary, quaternary and higher order materials and doped materials, such as, but not restricted to: BP, AlP, AlAs, AlSb; GaN, GaP, GaAs, GaSb, InN, InP, InAs, InSb, AlN, BN;

III-IV material incorporating a first element from group 13 of the periodic table and a second element from group 14 of the periodic table and also including ternary, quaternary and higher order materials and doped materials, such as, but not restricted to: $B_4C$, $Al_4C_3$, $Ga_4C$;

III-VI material incorporating a first element from group 13 of the periodic table and a second element from group 16 of the periodic table and also including ternary, quaternary and higher order materials and doped materials, such as, but not restricted to: $Al_2S_3$, $Al_2Se_3$, $Al_2Te_3$, $Ga_2S_3$, $Ga_2Se_3$, $In_2S_3$, $In_2Se_3$, $Ga_2Te_3$, $In_2Te_3$;

IV-VI material incorporating a first element from group 14 of the periodic table and a second element from group 16 of the periodic table and also including ternary, quaternary and higher order materials and doped materials, such as, but not restricted to: PbS, PbSe, PbTe, $Sb_2Te_3$, SnS, SnSe, SnTe;

material incorporating a first element from any group in the d-block of the periodic table, and a second element from group 16 of the periodic table, and optionally including any element from group 13 of the periodic table to form ternary, quaternary and higher order materials and doped materials, such as, but not restricted to: NiS, CrS, $CuInS_2$, $CuInSe_2$, $CuGaS_2$, $CuGaSe_2$, $Cu_2ZnSnS_4$.

The method of shell growth is unrestricted. Methods for shelling nanocrystal cores are well-known in the art. For example, the growth of a ZnS shell on InP core nanocrystals is described in U.S. Pat. No. 7,588,828 the contents of which are hereby incorporated by reference in their entirety.

There is growing concern regarding the use of heavy metals in consumer goods such as electronics products. The EU's Restriction of the Use of Certain Hazardous Substances (RoHS) Directive 2002/95/EC limits the amounts of heavy metals that can be used in electrical and electronic appliances. Similar legislation is being adopted across the globe. In some embodiments, the shell material is free of heavy metals. When the core of the nanoparticle contains one or more heavy metals, a heavy metal-free shell layer may prevent leaching of heavy metal ions from the core, which could be encountered, for example, in landfill environment or in biological systems.

When two or more types of the halide perovskite nanocrystals described herein are combined in a solution or matrix (for example a resin), the shell layer may act as a physical barrier to prevent anion exchange between the halide ions. This may enable two or more types (colors) of halide perovskite nanocrystals to be used to form, for example, a light-emitting device while retaining their distinct emissive properties. For example, green-emitting core/shell halide perovskite nanoparticles and red-emitting core/shell halide perovskite nanoparticles may be combined in a solution or matrix and incorporated into a device that emits white light when irradiated by a blue-emitting light source (such as a blue-emitting LED). Blue-, green- and red-emitting core/shell halide perovskite nanoparticles may be combined in a solution or matrix and incorporated into a device that emits white light when irradiated by an ultraviolet-emitting light source (such as an ultraviolet-emitting LED). Further, the shell layer may help to eliminate defects, dangling bonds and trap states from the halide perovskite core surface to improve the photoluminescence QY and stability of the nanocrystals.

EXAMPLES

Example 1. Synthesis of Core/Shell $CsPbBr_3$/ZnS Quantum Dots

First, a solution of Cs-oleate was prepared by mixing $Cs_2CO_3$ (0.407 g) with octadecene (20 mL) and oleic acid (1.55 mL), in a 50-mL 3-neck flask. The resulting mixture was dried for 1 hour at 120° C., and then heated under $N_2$ to 150° C. until all the $Cs_2CO_3$ was dissolved. The solution was kept at 140° C. to prevent solidifying.

$CsPbBr_3$ cores were synthesized by mixing $PbBr_2$ (69 mg) and octadecene (5 mL) in a 25-mL 3-neck flask. The cloudy suspension was heated to 120° C. under nitrogen. Subsequently, oleic acid (0.5 mL) and oleylamine (0.5 mL) were injected and the solution was stirred until the $PbBr_2$ dissolved completely. The reaction mixture was heated to 180° C. and Cs-oleate was injected. After 5 seconds, the cloudy, yellow mixture was cooled with compressed air. An aliquot of the crude solution had the following optical properties: photoluminescence maximum ($PL_{max}$)=507 nm, full-width at half-maximum (FWHM)=27.5 nm, photoluminescence quantum yield (PLQY)=36%. The reaction solution was centrifuged and the particles were precipitated by adding acetone to the supernatant. The resulting pellet was re-dispersed in hexane.

For the shelling, 1 mL of core solution was mixed with octadecene (5 mL), zinc acetate (36.7 mg) and dodecanethiol (0.12 mL) and the resulting mixture was degassed at room temperature for 5 minutes. The flask was refilled with nitrogen and heated to 180° C. Once the temperature reached 180° C., the reaction was cooled again. An aliquot of the crude solution had the following optical properties: $PL_{max}$=519 nm, FWHM=17 nm, PLQY=32%. The emission wavelength was significantly red-shifted compared to the un-passivated cores.

Example 2. Synthesis of Core/Shell $CsPbBr_3$/PbS QDs

First, a solution of Cs-oleate was prepared by mixing $Cs_2CO_3$ (0.407 g) with octadecene (20 mL) and oleic acid (1.55 mL), in a 50-mL 3-neck flask. The resulting mixture was dried for 1 hour at 120° C., and then heated under $N_2$ to 150° C. until all the $Cs_2CO_3$ was dissolved. The solution was kept at 140° C. to prevent solidifying.

$CsPbBr_3$ cores were synthesized by mixing $PbBr_2$ (69 mg) and octadecene (5 mL) in a 25-mL 3-neck flask. The cloudy suspension was heated to 120° C. under nitrogen. Subsequently, oleic acid (0.5 mL) and oleylamine (0.5 mL) were injected and the solution was stirred until the $PbBr_2$ dissolved completely. The reaction mixture was heated to 180° C. and Cs-oleate was injected. After 5 seconds, the cloudy, yellow mixture was cooled with compressed air. An aliquot of the crude solution had the following optical properties: $PL_{max}$=507 nm, FWHM=27.5 nm, PLQY=36%. The reaction solution was centrifuged and the particles were precipitated by adding acetone to the supernatant. The resulting pellet was re-dispersed in hexane.

For the shelling, 0.4 mL of core solution was mixed with octadecene (5 mL) and dodecanethiol (0.2 mL) and the resulting mixture was degassed at room temperature for 5 minutes. The flask was refilled with nitrogen and heated to 120° C. Once the temperature reached 120° C., the reaction was held for 10 minutes before cooling to room temperature. An aliquot of the crude solution had the following optical properties: $PL_{max}$=520 nm, FWHM=18 nm, PLQY=21%. The emission wavelength was significantly red-shifted compared to the un-passivated cores.

Example 3. Synthesis of Core/Shell $CsPbBr_3$/PbS Quantum Dots

First, a solution of Cs-oleate was prepared by mixing $Cs_2CO_3$ (0.407 g) with octadecene (20 mL) oleic acid (1.55 mL), into a 50-mL 3-neck flask. The resulting mixture was dried for 1 hour at 120° C., and then heated under $N_2$ to 150° C. until all the $Cs_2CO_3$ dissolved. The solution was kept at 140° C. to prevent solidifying.

$CsPbBr_3$ cores were synthesized by mixing $PbBr_2$ (69 mg) and octadecene (5 mL) in a 25-mL 3-neck flask. The cloudy suspension was heated to 120° C. under nitrogen. Subsequently, oleic acid (0.5 mL) and oleylamine (0.5 mL) were injected and the solution was stirred until the $PbBr_2$ dissolved completely. The reaction mixture was heated to 180° C. and Cs-oleate was injected. After 5 seconds, the cloudy, yellow mixture was cooled with compressed air. An aliquot of the crude solution had the following optical properties: $PL_{max}$=512 nm, FWHM=20 nm, PLQY=31%. The reaction solution was centrifuged and the particles were precipitated by adding acetone to the supernatant. The resulting pellet was re-dispersed in hexane.

Figure 2:
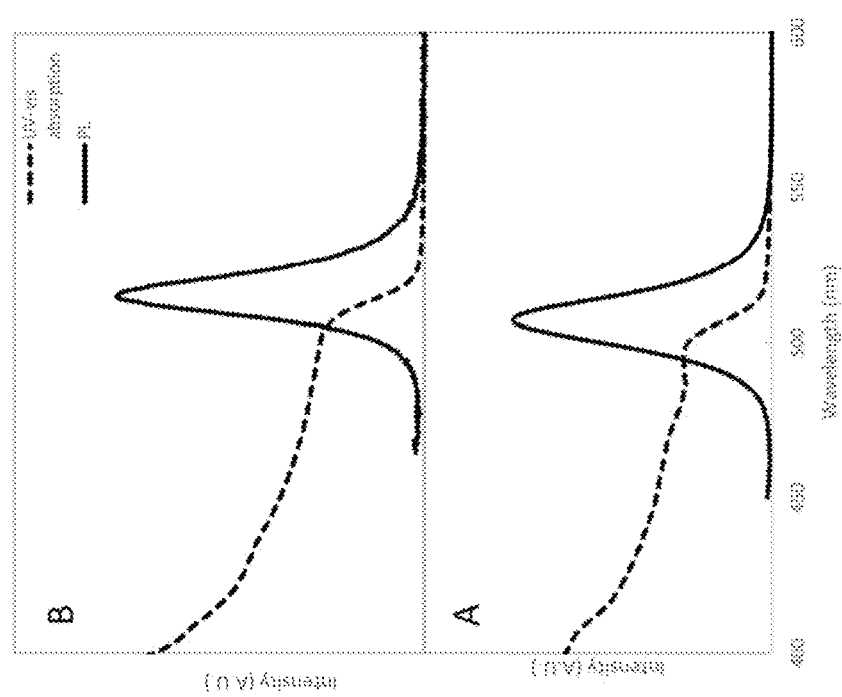
FIG. 2 shows UV-vis and PL spectra of (A) cores and (B) core/shell nanoparticles. The UV-vis exciton peak and the emission wavelength of the core/shell material are red-shifted compared to the un-passivated cores.

For the shelling, 1 mL of core solution was mixed with octadecene (3 mL), $PbBr_2$ (73 mg) and dodecanethiol (0.2 mL) and the resulting mixture was degassed at room temperature for 5 minutes. The flask was refilled with nitrogen and heated to 180° C. Once the temperature reached 120° C., the reaction was held at this temperature for 30 minutes and cooled again. An aliquot of the crude solution had the following optical properties: $PL_{max}$=514 nm, FWHM=19 nm, PLQY=83%. The emission wavelength was slightly red-shifted and the PLQY increased significantly compared to the un-passivated cores. The UV-vis and PL spectra of core and core/shell species are shown in FIG. 2.

By enabling two or more types of halide perovskite nanocrystals to be processed together, the present invention allows such nanocrystals to be processed more easily, and at lower cost, than prior art methods wherein each type of halide perovskite nanocrystal must be separately encapsulated prior to mixing.

All-inorganic perovskite nanoparticles are unstable in polar solvents, while organometallic halide perovskite nanoparticles are unstable in the presence of humidity and high temperatures [H. C. Yoon, H. Kang, S. Lee, J. H. Oh, H. Yang and Y. R. Do, *ACS Appl. Mater. Interfaces,* 2016, 8, 18189]. The addition of a non-halide perovskite shell layer to the halide perovskite core nanoparticles may help to overcome some of these stability issues.

The foregoing presents particular embodiments embodying the principles of the invention. Those skilled in the art will be able to devise alternatives and variations which, even if not explicitly disclosed herein, embody those principles and are thus within the scope of the invention. Although particular embodiments of the present invention have been shown and described, they are not intended to limit what this patent covers. One skilled in the art will understand that various changes and modifications may be made without departing from the scope of the present invention as literally and equivalently covered by the following claims.

What is claimed is:

1. A photoluminescent core/shell semiconductor nanoparticle comprising:
a core comprising a halide perovskite semiconductor of the form $ABX_3$; and
a shell substantially surrounding the core and comprising $BaTiO_3$, $SrTiO_3$, $BiFeO_3$, $LaNiO_3$, $CaTiO_3$, $PbTiO_3$ or $LaYbO_3$, wherein
the shell is substantially free of halide perovskites,
A is selected from the group consisting of $Li^+$, $Na^+$, $K^+$, $Rb^+$ and $Cs^+$,
M is a divalent metal cation selected from the group consisting of $Mg^{2+}$, $Mn^{2+}$, $Pb^{2+}$, $Sn^{2+}$ and $Zn^{2+}$, and
X is selected from the group consisting of $F^-$, $Cl^-$, $Br^-$ and $I^-$.

2. A composition comprising:
a population of core/shell semiconductor nanoparticles according to claim 1; and
a matrix.

3. The composition of claim 2, wherein the matrix comprises a resin.

4. A solution comprising:
a population of core/shell semiconductor nanoparticles according to claim 1; and
a solvent.

5. A light-emitting device comprising the photoluminescent core/shell nanoparticle of claim 1.

* * * * *